(12) United States Patent
Hoss et al.

(10) Patent No.: US 12,722,016 B2
(45) Date of Patent: Sep. 1, 2026

(54) CONFORMAL ANTENNA FOR AN IMPLANTABLE MEDICAL DEVICE

(71) Applicant: NeuroPace, Inc., Mountain View, CA (US)

(72) Inventors: Alister Hoss, Sherman Oaks, CA (US); Tygo A. Ebenhahn, San Francisco, CA (US); Natalya A. Bruner, Santa Cruz, CA (US); Stephen T. Archer, Sunnyvale, CA (US)

(73) Assignee: NeuroPace, Inc., Mountain View, CA (US)

( * ) Notice: Subject to any disclaimer, the term of this patent is extended or adjusted under 35 U.S.C. 154(b) by 531 days.

(21) Appl. No.: 18/124,222

(22) Filed: Mar. 21, 2023

(65) Prior Publication Data

US 2024/0316350 A1 Sep. 26, 2024

(51) Int. Cl.
*A61N 1/37* (2006.01)
*A61N 1/372* (2006.01)
*A61N 1/375* (2006.01)

(52) U.S. Cl.
CPC ......... *A61N 1/37229* (2013.01); *A61N 1/375* (2013.01)

(58) Field of Classification Search
CPC ............ A61N 1/37229; A61N 1/37211; A61N 1/37217; A61N 1/37223
See application file for complete search history.

(56) References Cited

U.S. PATENT DOCUMENTS 6,708,065 B2 3/2004 Von Arx et al.
6,810,285 B2 10/2004 Pless et al.
7,103,408 B2 9/2006 Haller et al.
7,120,992 B2 10/2006 He et al.
7,132,173 B2 11/2006 Daulton
7,177,698 B2 2/2007 Klosterman et al.
7,317,946 B2 1/2008 Twetan et al.
7,351,921 B1 4/2008 Haller et al.
7,428,438 B2 9/2008 Parramon et al.
7,437,193 B2 10/2008 Parramon et al.
7,467,014 B2 12/2008 Fuller et al.
7,483,752 B2 1/2009 Von Arx et al.
7,587,241 B2 9/2009 Parramon et al.
7,640,061 B2 12/2009 He et al.
(Continued)

OTHER PUBLICATIONS

International Search Report & Written Opinion, PCT/US2024/014941, Apr. 18, 2024, 10 pgs.
(Continued)

*Primary Examiner* — Eric D. Bertram
(74) *Attorney, Agent, or Firm* — LOZA & LOZA, LLP; David S. Sarisky

(57) ABSTRACT

An implantable medical device (IMD) configured for implant in a body includes an enclosure that houses communication circuitry, an antenna, a dielectric layer, and a transmission line. The enclosure includes an outer surface configured to be oriented in a direction facing the exterior of the body and to be placed adjacent tissue. The antenna includes a ground plane corresponding to the enclosure, a dielectric spacer that conforms to the outer surface of the enclosure, and a radiating element that conforms to the dielectric spacer. The dielectric layer overlays the radiating element and the dielectric spacer. The transmission line is electrically connected between the radiating element and the communication circuitry.

17 Claims, 13 Drawing Sheets

(56) References Cited

U.S. PATENT DOCUMENTS 7,766,216 B2 8/2010 Daulton
7,781,683 B2 8/2010 Haller et al.
7,822,480 B2 10/2010 Park et al.
7,903,043 B2* 3/2011 Rawat .................. H01Q 1/2208 343/873
7,904,167 B2 3/2011 Klosterman et al.
8,032,227 B2 10/2011 Parramon et al.
8,127,424 B2 3/2012 Haller et al.
8,185,212 B2 5/2012 Carbunaru et al.
8,386,048 B2 2/2013 Mcclure et al.
8,543,216 B2 9/2013 Carbunaru et al.
8,547,248 B2 10/2013 Zdeblick et al.
8,571,679 B2 10/2013 Parramon et al.
8,655,451 B2 2/2014 Klosterman et al.
8,670,835 B2 3/2014 Park et al.
8,755,899 B2 6/2014 Von Arx et al.
8,914,129 B2 12/2014 Parramon et al.
9,079,041 B2 7/2015 Park et al.
9,089,712 B2 7/2015 Joshi et al.
9,162,071 B2 10/2015 Parramon et al.
9,240,630 B2 1/2016 Joshi
9,242,106 B2 1/2016 Klosterman et al.
9,259,582 B2 2/2016 Joshi et al.
9,265,958 B2 2/2016 Joshi et al.
9,270,011 B2 2/2016 Joshi
9,399,143 B2 7/2016 Yamamoto et al.
9,700,731 B2 7/2017 Nassif et al.
9,837,704 B2 12/2017 Andersen et al.
9,950,163 B2 4/2018 Meskens et al.
10,014,571 B2 7/2018 Andersen et al.
10,186,760 B2 1/2019 Heppell
10,193,217 B2 1/2019 Andersen et al.
10,220,215 B2 3/2019 Howard
10,299,681 B2 5/2019 Hess
10,957,970 B2 3/2021 Li et al.
11,040,209 B2 6/2021 Aghassian et al.
11,040,210 B2 6/2021 Lim et al.
11,245,181 B2 2/2022 Heppell
11,283,161 B2 3/2022 Zhao
11,351,388 B1 6/2022 O'Driscoll et al.
2002/0123776 A1 9/2002 Von Arx et al.
2004/0058186 A1 3/2004 Daulton
2004/0059392 A1 3/2004 Parramon et al.
2004/0088032 A1 5/2004 Haller et al.
2004/0098068 A1 5/2004 Carbunaru et al.
2004/0176811 A1 9/2004 Von Arx et al.
2005/0021108 A1 1/2005 Klosterman et al.
2005/0057905 A1 3/2005 He et al.
2005/0119716 A1 6/2005 Mcclure et al.
2005/0131494 A1 6/2005 Park et al.
2005/0131495 A1 6/2005 Parramon et al.
2005/0203583 A1 9/2005 Twetan et al.
2006/0247712 A1* 11/2006 Fuller ................ A61N 1/37229 607/32
2007/0032839 A1 2/2007 Parramon et al.
2007/0057025 A1 3/2007 Daulton
2007/0073360 A1 3/2007 He et al.
2007/0135867 A1 6/2007 Klosterman et al.
2008/0121419 A1 5/2008 Haller et al.
2008/0306359 A1 12/2008 Zdeblick et al.
2009/0192574 A1 7/2009 Von Arx et al.
2009/0292341 A1 11/2009 Parramon et al.
2010/0114245 A1* 5/2010 Yamamoto ........... H01Q 1/2283 343/873
2010/0249886 A1 9/2010 Park et al.
2010/0293774 A1 11/2010 Haller et al.
2010/0298910 A1 11/2010 Carbunaru et al.
2011/0137378 A1 6/2011 Klosterman et al.
2011/0313490 A1 12/2011 Parramon et al.
2012/0197352 A1 8/2012 Carbunaru et al.
2012/0276854 A1 11/2012 Joshi et al.
2012/0276856 A1 11/2012 Joshi et al.
2012/0287004 A1 11/2012 Joshi et al.
2013/0207863 A1 8/2013 Joshi
2014/0051965 A1 2/2014 Zdeblick et al.
2014/0052218 A1 2/2014 Parramon et al.
2014/0107734 A1 4/2014 Park et al.
2014/0236263 A1 8/2014 Klosterman et al.
2014/0266921 A1 9/2014 Joshi
2014/0266933 A1 9/2014 Andersen et al.
2015/0066112 A1 3/2015 Parramon et al.
2016/0087331 A1 3/2016 Heppell
2016/0199658 A1* 7/2016 Nassif ............... H04W 72/0453 29/601
2017/0056656 A1* 3/2017 Meskens .............. A61N 1/3754
2017/0281957 A1 10/2017 Howard
2018/0020919 A1 1/2018 Hess
2018/0040944 A1 2/2018 Andersen et al.
2018/0069303 A1 3/2018 Li et al.
2018/0200527 A1 7/2018 Aghassian et al.
2018/0277938 A1 9/2018 Andersen et al.
2019/0123430 A1 4/2019 Heppell
2019/0299014 A1* 10/2019 Lim ................... A61N 1/37229
2021/0021020 A1* 1/2021 Zhao .................. A61N 1/37229
2021/0167488 A1 6/2021 Li et al.
2021/0220655 A1 7/2021 Aghassian et al.
2021/0268295 A1 9/2021 Lim et al.
2022/0209395 A1 6/2022 Zhao
2024/0021975 A1* 1/2024 Al-Sehemi ............... H01Q 1/12

OTHER PUBLICATIONS

International Preliminary Report on Patentability, International Patent Application No. PCT/US2024/014941, Oct. 2, 2025, 8 pgs.

* cited by examiner 216a
102
2B
2C
206
202
204
210
2B
201
Z
2C
208
216b
X
Y
212b
212a
214b
214a 208
210
220
206
204

R88.4
R62.5

208
210
220
206
204

R102
R102

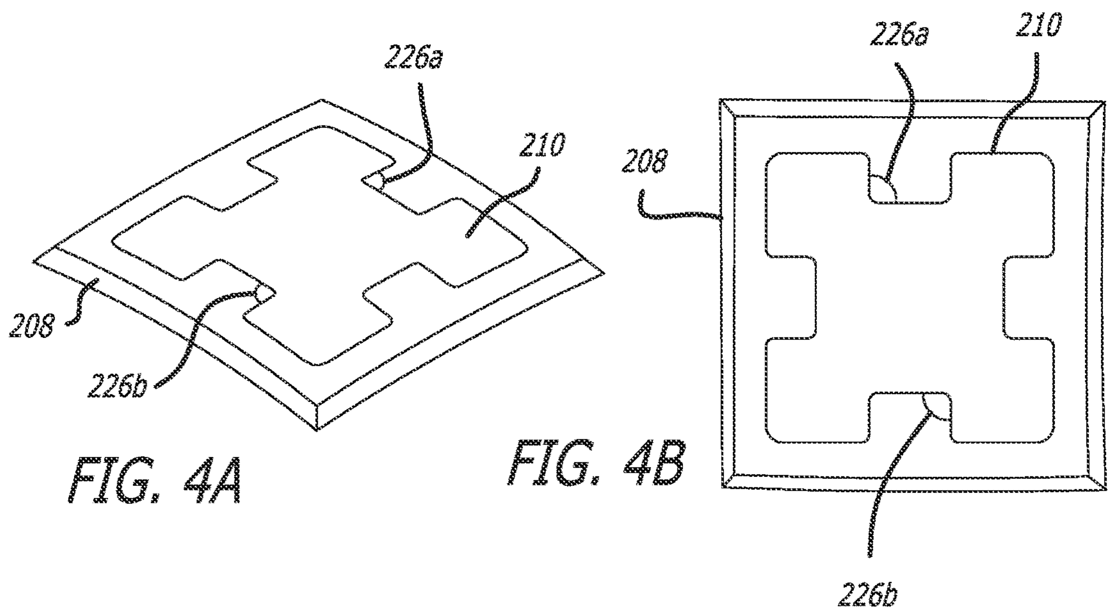
FIG. 4A
FIG. 4B
FIG. 4C
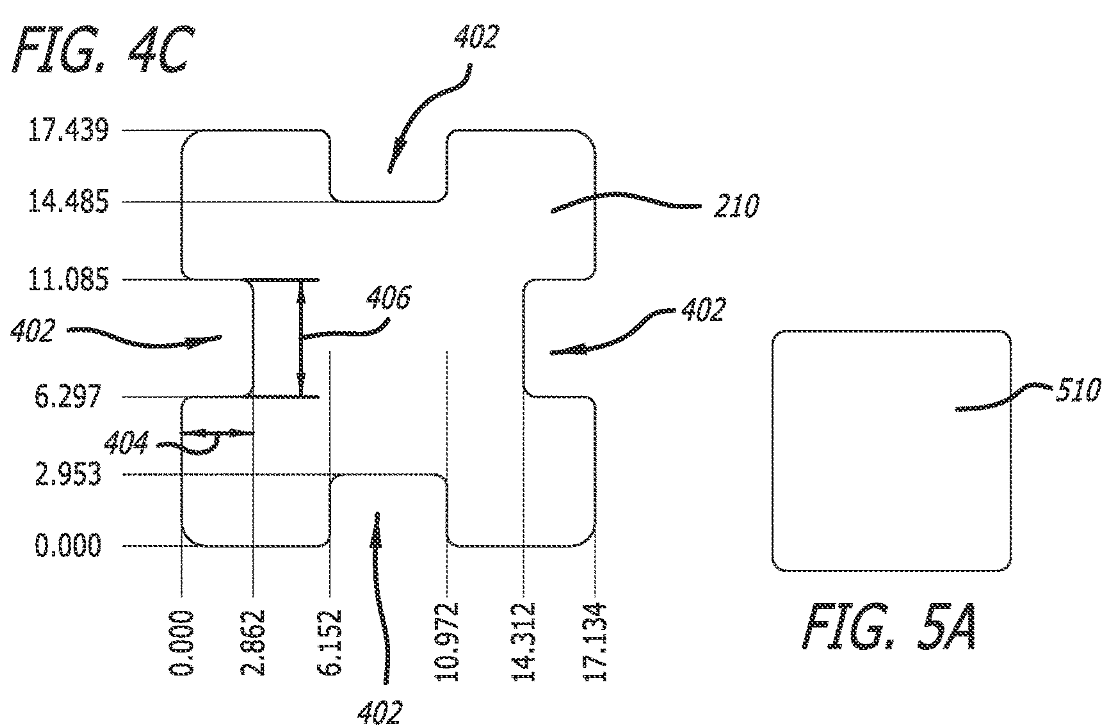
FIG. 5A
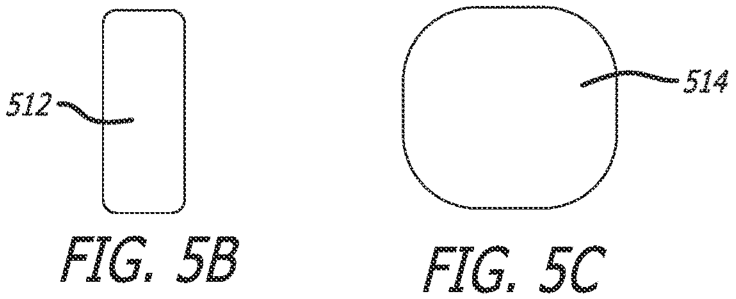
FIG. 5B
FIG. 5C

Frequency (GHz)
Return Loss (dB)
0
-10
-20
-30
-40
-50
-60
0.5 0.69 0.88 1.07 1.26 1.45 1.64 1.83 2.02 2.21 2.4 2.59 2.78 2.97 3.16 3.35 3.54 3.73 3.92 4.11 4.3 4.49 4.68 4.87
Matching the pin
BLE board/PCB
Matching the pin
coming out of the can Frequency (GHz)
Insertion Loss (dB)
0
-0.05
-0.1
-0.15
-0.2
-0.25
-0.3
-0.35
0.5 0.69 0.88 1.07 1.26 1.45 1.64 1.83 2.02 2.21 2.4 2.59 2.78 2.97 3.16 3.35 3.54 3.73 3.92 4.11 4.3 4.49 4.68 4.87

Frequency (GHz)
Radiated emission from ITL (dBm)
-52
-52.5
-53
-53.5
-54
-54.5
2.4 2.41 2.42 2.43 2.44 2.45 2.46 2.47 2.48 2.49 2.5

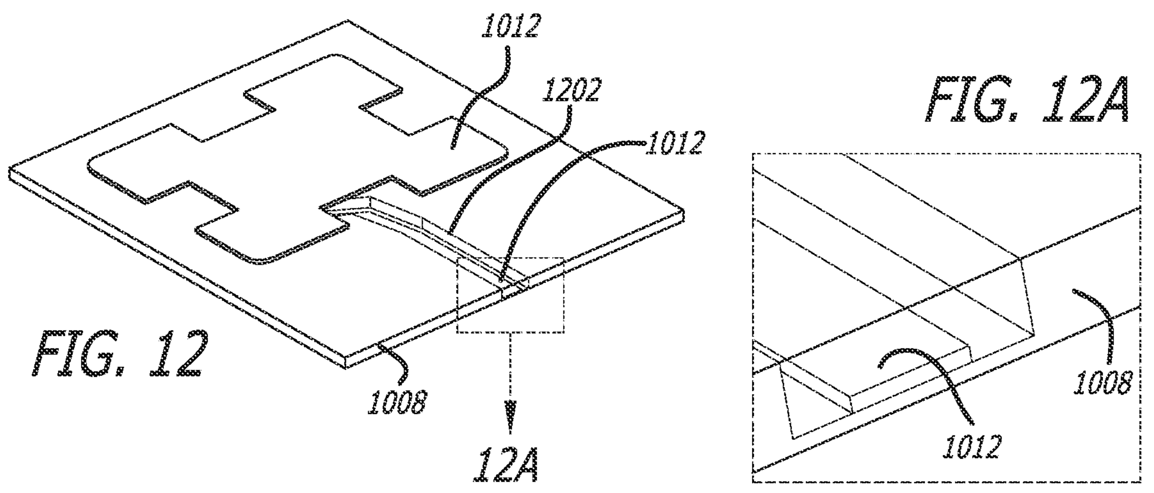
FIG. 12
FIG. 12A
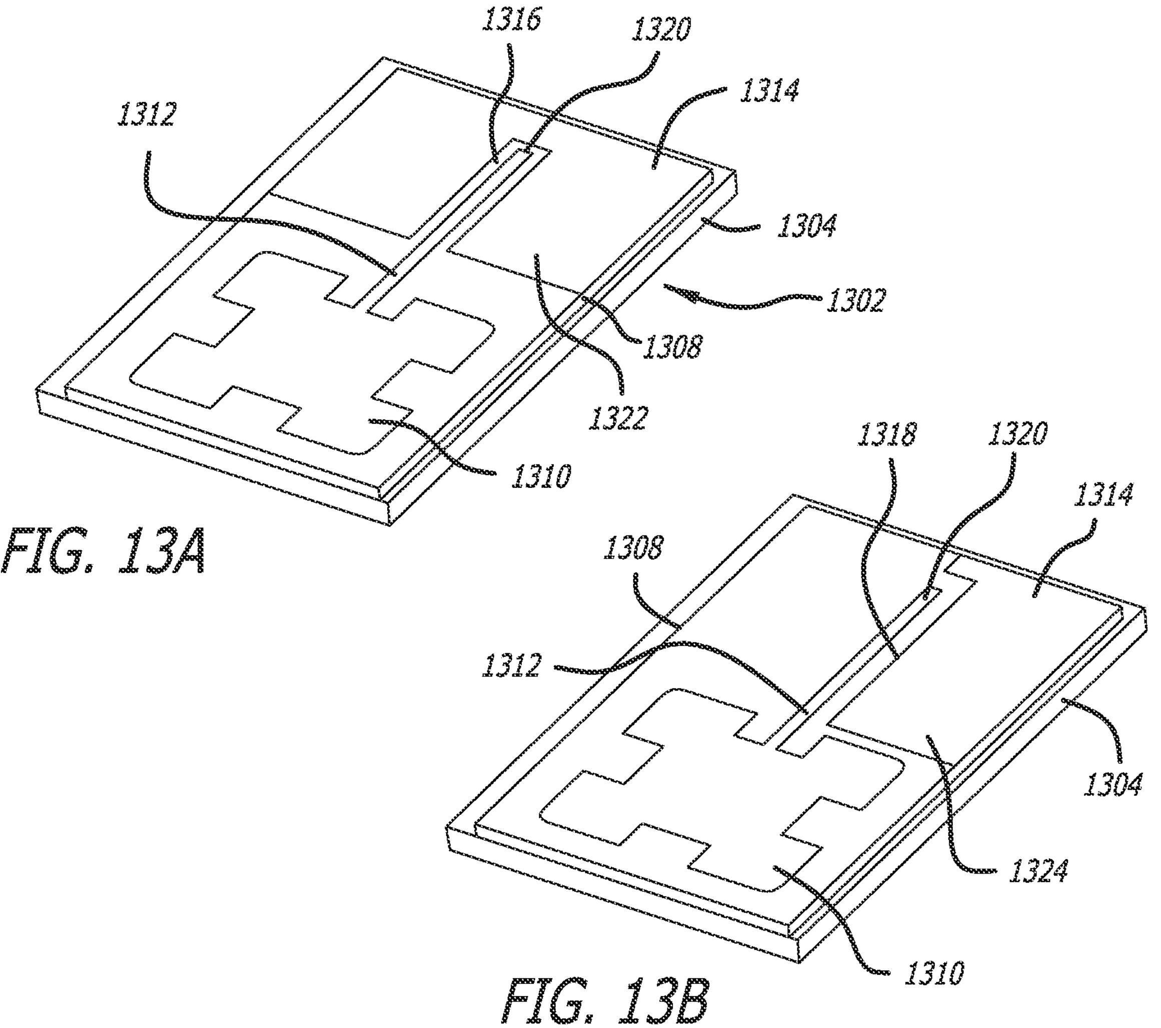
FIG. 13A
FIG. 13B

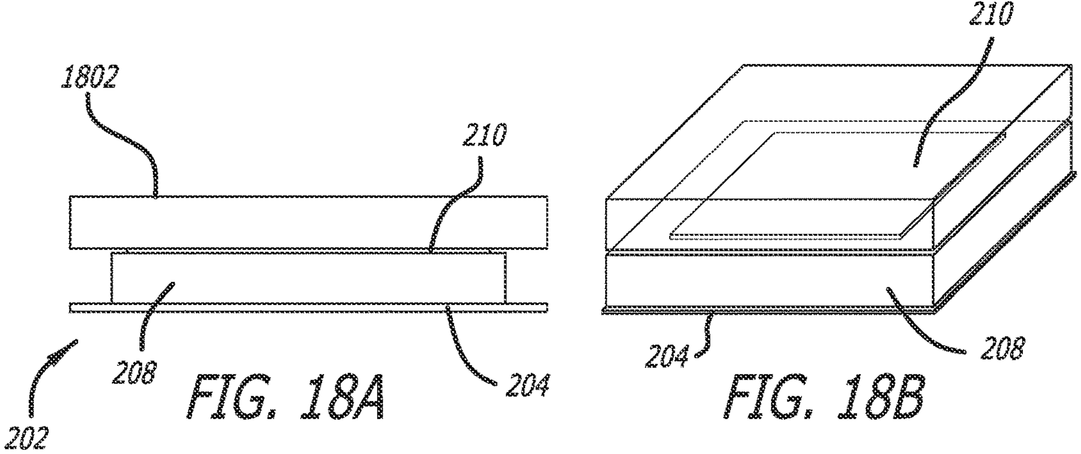
FIG. 18A
FIG. 18B
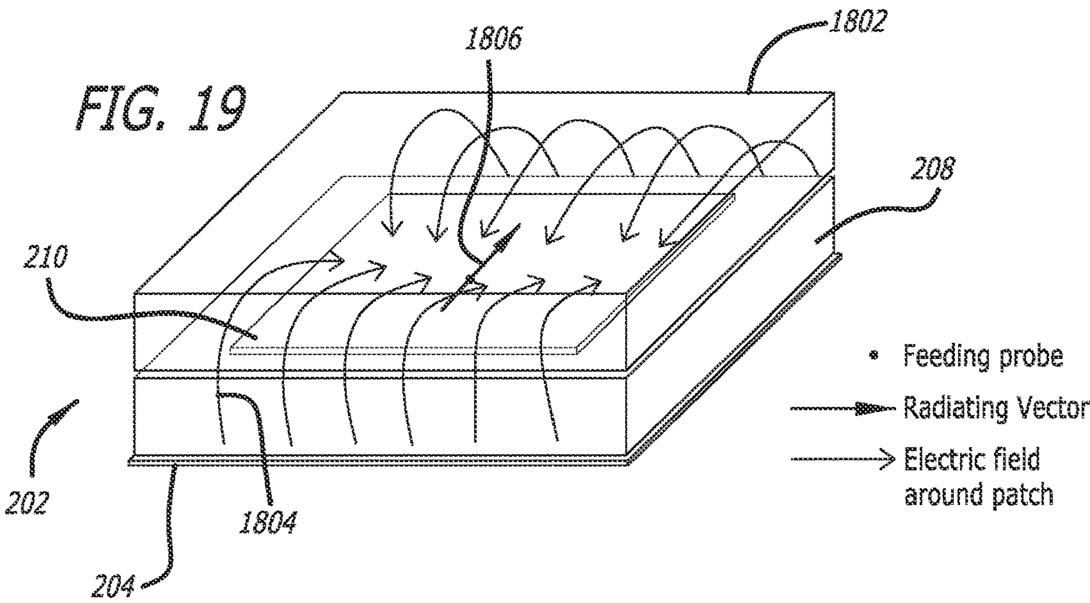
FIG. 19
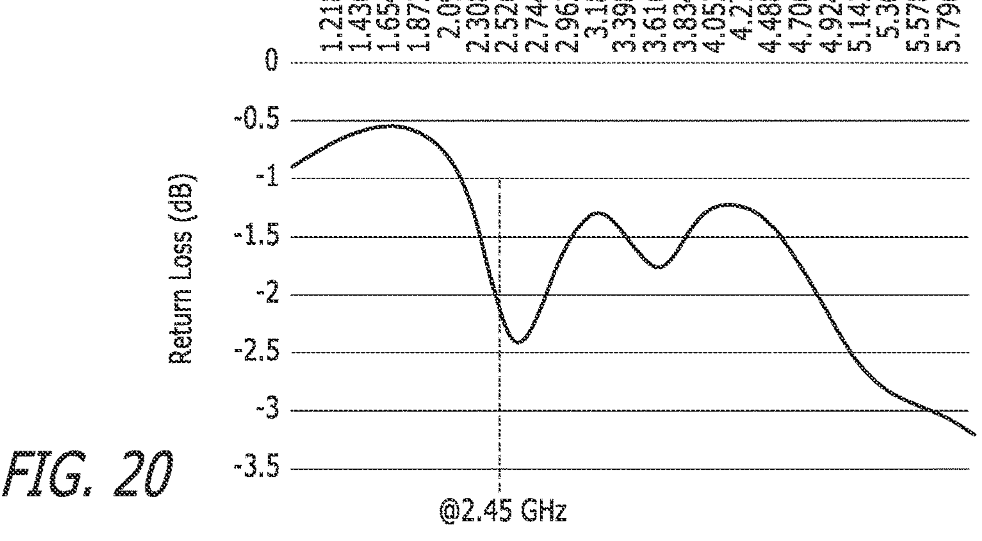
FIG. 20

CONFORMAL ANTENNA FOR AN IMPLANTABLE MEDICAL DEVICE

TECHNICAL FIELD

The present disclosure relates generally to antennas for implantable medical devices, and more particularly, to conformal antennas associated with a surface of an enclosure or housing of an implantable medical device.

BACKGROUND

Active implantable medical devices are known that can be configured to communicate with external components wirelessly, such as via a form of telemetry. The communication may be desirable to, for example, download information acquired by and stored on the implanted medical device to an external component, such as patient-controlled external component. Alternatively, or additionally, an external component configured as a programmer may be brought into communication with the implantable medical device to obtain data from the device or to send data to the device from the programmer, such as new programming instructions that control whatever it may be that the implantable medical device is configured to do. For example, the implantable medical device may be programmed to measure electrographic signals sensed from the patient and/or detect electrographic events whenever such events occur in the electrographic signals, or deliver a form of electrical stimulation to the patient.

A communication link between the implantable medical device and an external apparatus may be established with an intermediate device, such as wand for near-field or short-range telemetry. For example, the implantable medical device may have a telemetry coil that enables transmission and reception of signals, to or from an external apparatus, via inductive coupling. Alternatively, a communication link between the implantable medical device and an external component may be established with an antenna for a radio frequency (RF) link. Far field or long-range telemetry may obviate the need for the intermediate device (e.g., the wand) and allow the external apparatus to be further away from the implantable medical device than is the case with near-field telemetry.

SUMMARY

An implantable medical device (IMD) configured for implant in a body includes an enclosure that houses communication circuitry, an antenna, a dielectric layer, and a transmission line. The enclosure includes an outer surface configured to be oriented in a direction facing the exterior of the body and to be placed adjacent tissue. The antenna includes a ground plane corresponding to the enclosure, a dielectric spacer that conforms to the outer surface of the enclosure, and a radiating element that conforms to the dielectric spacer. The dielectric layer overlays the radiating element and the dielectric spacer. The transmission line is electrically connected or coupled between the radiating element and the communication circuitry.

It is understood that other aspects of apparatuses and methods will become readily apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of apparatuses and methods will now be presented in the detailed description by way of example, and not by way of limitation, with reference to the accompanying drawings, wherein:

FIGS. 4A and 4B are illustrations of the conformal antenna of FIG. 3A.

FIG. 4C is an illustration of the radiating element of the conformal antenna of FIG. 3A.

FIGS. 5A-5C are schematic illustrations of some possible configurations of a radiating element of a conformal antenna.

FIG. 12 is an illustration of components of a conformal antenna and an external transmission line within a channel or trench of a dielectric substrate of the antenna.

FIG. 12A is a detailed blow up of the area indicated as 12A in FIG. 12.

FIGS. 13A and 13B are illustrations of components of a conformal antenna and an external transmission lines on a dielectric substrate of the antenna and coplanar with a radiating element of the antenna.

FIGS. 18A and 18B are schematic illustration of a conformal antenna.

FIG. 19 is a schematic illustration of active electric fields generated by the conformal antenna of FIGS. 18A and 18B.

FIG. 20 is a graph of return loss as a function of frequency for the traditional patch antenna of FIGS. 18A and 18B.

DETAILED DESCRIPTION

Figure 1:
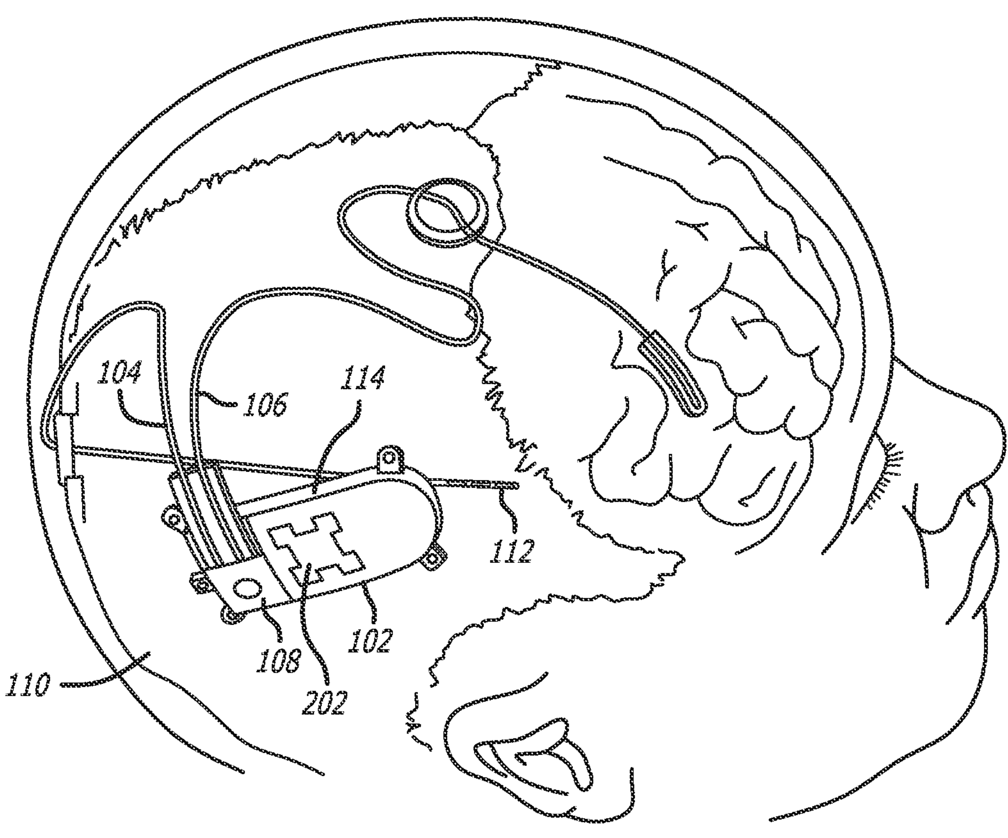
FIG. 1 is perspective, schematic illustration of a neurostimulation system implanted in a patient, including a neurostimulator with a conformal antenna and a pair of leads.

With reference to FIG. 1, an example implantable medical system in the form of a neurostimulation system is implanted in a patient. The neurostimulation system includes an implantable medical device (IMD), referred to going forward as a neurostimulator 102, and two electrode-bearing brain leads 104, 106. The neurostimulation system is configured to sense and record electrical brain activity, to detect electrographic events in the electrical brain activity, and to deliver responsive neurostimulation therapy. Responsive neurostimulation systems are described in, for example, U.S. Pat. No. 6,016,449 to Fischell, et al. for "System for Treatment of Neurological Disorders", issued Jan. 18, 2000, U.S. Pat. No. 6,810,285 to Pless et al. for "Seizure Sensing and Detection Using an Implantable Device," issued Oct. 24, 2004, and U.S. Pat. No. 6,690,974 to Archer et al. for "Stimulation Signal Generator for an Implantable Device" issued Feb. 10, 2004. Each of the '449, '285 and '974 patents is hereby incorporated by reference in the entirety.

The neurostimulator 102 is configured to be secured in an opening formed through the cranium 110. To this end, a tray or ferrule 114 is placed in the opening and secured to the cranium, and the neurostimulator 102 is placed in the ferrule. The neurostimulator 102 is oriented in the ferrule 114 such that a conformal antenna 202 of the neurostimulator faces outward from the interior of the cranium and is positioned to be adjacent the patient's scalp tissue.

With continued reference to FIG. 1, the neurostimulator 102 includes a lead connector 108 adapted to receive one or more of the brain leads, such as a deep brain or depth lead 104 and a cortical strip lead 106. The depth lead is implanted so that a distal end of it is situated within the patient's neural tissue, whereas the cortical strip lead is implanted under the dura mater so that a distal end of it rests on a surface of the brain. The lead connector 108 acts to physically secure the brain leads 104, 106 to the neurostimulator 102, and facilitates electrical connection to conductors in the brain leads 104, 106 coupling one or more electrodes at or near a distal end of the lead to circuitry within the neurostimulator 102.

The proximal portion of the deep brain lead 104 is generally situated on the outer surface of the cranium 110 (and under the patient's scalp), while the distal portion of the lead enters the cranium and is coupled to at least one depth electrode 112 implanted in a desired location in the patient's brain. The proximal portion of the cortical lead 106 is generally situated on the outer surface of the cranium 110 (and under the patient's scalp), while the distal portion of the lead enters the cranium. The distal portion of the cortical lead 106 includes at least one cortical electrode (not visible) implanted in a desired location on the patient's brain. Long-range (wireless) telemetry is a form of communication between implantable medical devices (IMD) and external programmers and monitors. This communication can take place over several meters or even across rooms. Previous generation of systems used near-field inductive telemetry to communicate from implanted device to external programmer. In modern and emerging systems, radio frequencies are used for long-range telemetry allowing much longer distances of communication. Along with radio frequencies comes the demand for better, high-tuned antennas to support long-range telemetry.

IMD Communication

An international standard for implant communication is the Medical Implant Communication Service) MICS, which operates at 401-406 MHz [ETSI, 2002]. Due to the frequency of this signal and the limited power restrictions imposed by the standard, antennas used for this communication must reside outside of the protective metal housing used in most IMDs.

Most antenna designs for IMDs are placed just outside the metal housing but within rigid encapsulation, such as epoxy, to keep the antenna structure rigid and immobile. Often this is desirable since the shape and length of the antenna can have a profound effect on the performance of the antenna. The main criterion for the performance of an antenna is its efficiency in converting electrical current into electromagnetic power. The antenna is connected to the internal hermetically sealed electronics by an insulator-to-metal feedthrough (where the insulator may be formed of a material such as a ceramic or glass). Feedthrough structures bridge the hermetic barrier.

Disclosed herein is an IMD, e.g., a neurostimulator, with a conformal antenna formed in part by an enclosure of the neurostimulator, and other components that conform to an outer surface of the enclosure. In some embodiments, a radiating element of the antenna conforms to an outer surface of the enclosure and is coupled to communication circuitry inside the enclosure by an internal transmission line. In some embodiments, a radiating element of the antenna conforms to an outer surface of the enclosure and is coupled to communication circuitry inside the enclosure by an external transmission line that conforms to, and extends along, an outer surface of the enclosure.

The conformal antenna is configured to provide efficient radiation in two or more frequency bands in a particular operating environment, wherein the conformal antenna is adjacent to biological tissue. The two frequency bands of interest are the 2.4 GHz spectrum band (2400 to 2483.5 MHz) (e.g., Bluetooth) and the 5.8 GHz spectrum band (5.15 GHz to 5.85 GHZ) (e.g., WiFi). The antenna is also configured with a radiating element that radiates with a single or dual polarizations.

Internal Transmission Line

Figure 2A:
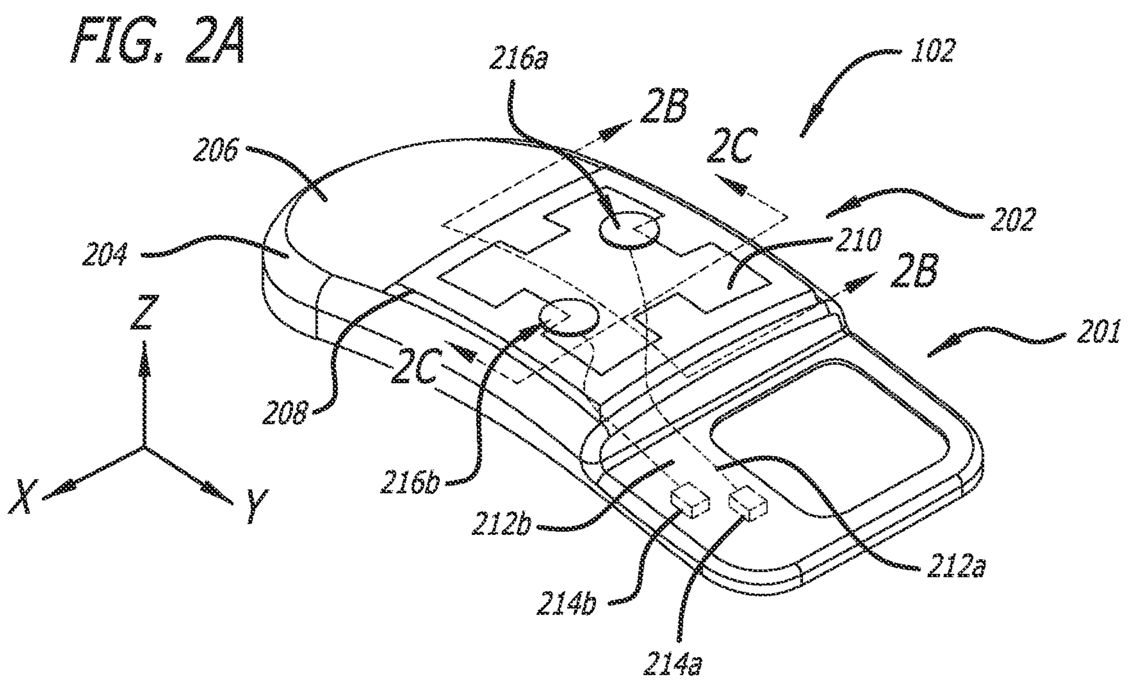
FIG. 2A is an illustration of a neurostimulator with a conformal antenna and internal transmission lines between the antenna and circuitry.
Figure 2B:
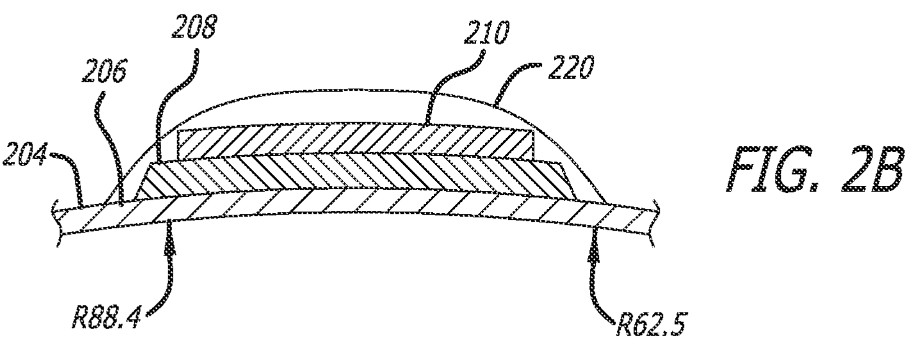
FIG. 2B is a schematic cross-section of the neurostimulator taken along line 2B-2B of FIG. 2A that shows elements of a conformal antenna.
Figure 2C:
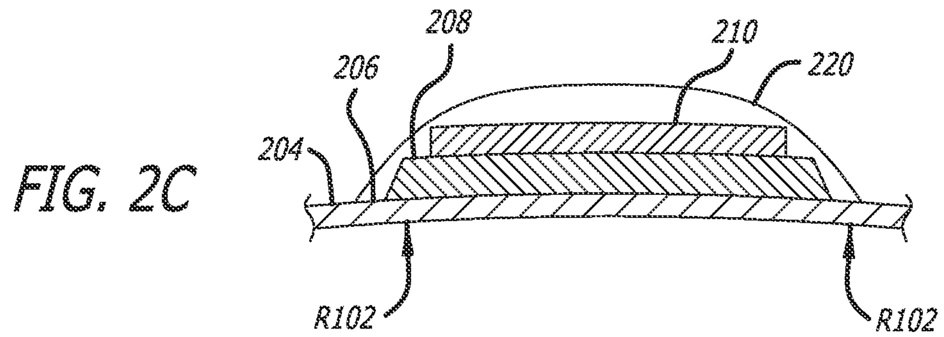
FIG. 2C is a schematic cross-section of the neurostimulator taken along line 2C-2C of FIG. 2A that shows elements of a conformal antenna.

FIG. 2A is an illustration of a neurostimulator 102 with a conformal antenna 202 that includes a radiating element that conforms to an outer surface of the enclosure and is coupled to communication circuitry inside the enclosure by an internal transmission line. Some components of the neurostimulator 102 are not shown in FIG. 2A for clarity in illustrating the conformal antenna 202. For example, a connector feedthrough is not included the portion 201 of the neurostimulator 102 where the lead connector 108 couples to the neurostimulator. FIG. 2B is a schematic cross-section illustration of the neurostimulator 102 along line yz of FIG. 2A that shows elements of the conformal antenna 202. FIG. 2C is a schematic cross-section illustration of the neurostimulator 102 along line xz of FIG. 2A that shows elements of the conformal antenna 202.

With reference to FIGS. 2A, 2B, and 2C, the neurostimulator 102 includes an enclosure 204 having an outer surface 206. As shown in FIG. 1, when the neurostimulator 102 is implanted, the outer surface 206 is oriented in a direction facing the exterior of the body, and is adjacent tissue. The enclosure 204 contains electronic circuitry. For example, first communication circuitry 214*a* and second communication circuitry 214*b* may be housed within the enclosure 204. The conformal antenna 202 includes a ground plane corresponding to the enclosure 204, a dielectric spacer 208 that conforms to, and is supported by, a portion of the outer surface of the enclosure, and a radiating element 210 that conforms to, and is supported by a portion of the dielectric spacer. With reference to FIGS. 2B and 2C, a dielectric layer 220 overlays the radiating element 210, the dielectric spacer 208, and a portion of the outer surface 206 of the enclosure 204.

Dual antenna feedthroughs 216*a*, 216*b* are electrically coupled to the radiating element 210 and extend through the enclosure 204 at a location adjacent the radiating element. A respective transmissions line 212*a*, 212*b* is electrically coupled to a respective one of the antenna feedthroughs 216*a*, 216*b* to thereby provide an electrical coupling between a respective one of communication circuitry 214*a*, 214*b* and the radiating element 210.

The dual feedthrough design allows the radiating element 210 to be fed from different communications circuitry at different locations within the enclosure 204 to provide multi-band performance. For example, the first communication circuitry 214*a* may support Bluetooth communication, while the second communication circuitry 214*b* supports Wi-Fi communication.

With reference to FIGS. 2B and 2C, each of 1) the enclosure 204 wall comprising the outer surface 206 that supports the dielectric spacer 208, 2) the dielectric spacer 208, and 3) the radiating element 210 is non-planar. In other words, each of the structures (the enclosure 204 wall, the dielectric spacer 208, and the radiating element 210) has a non-linear profile that is characterized by a respective curvature. In some embodiments, these respective curvatures are substantially the same or generally corresponds to each other. Stated another way with respect to the outer surface 206 of the enclosure 204 that supports the dielectric spacer 208 and the radiating element 210, the outer surface 206 may be characterized by a non-linear profile having a first curvature and the radiating element 210 may be characterized by a non-linear profile having a second curvature that generally corresponds to the first curvature. "Generally corresponds to" as used herein means the first curvature and the second curvature are not necessarily exactly the same and that a variation between the respective curvatures is within a tolerance, e.g., less a few mils (less than 0.1 mm). For example, with reference to FIG. 2B, in one configuration the respective curvatures of the enclosure 204 wall comprising the outer surface 206, the dielectric spacer 208, and the radiating element 210 along line 2B-2B through the conformal antenna 202 has a radius of curvature R88.4 at one end of this cross-section that transitions to a radius of curvature R62.5 at the other end of the cross-section. With reference to FIG. 2C, in one configuration the respective curvatures of the enclosure 204 wall comprising the outer surface 206, the dielectric spacer 208, and the radiating element 210 along line 2C-2C through the conformal antenna 202 has a radius of curvature R102 along this cross-section.

Figure 3A:
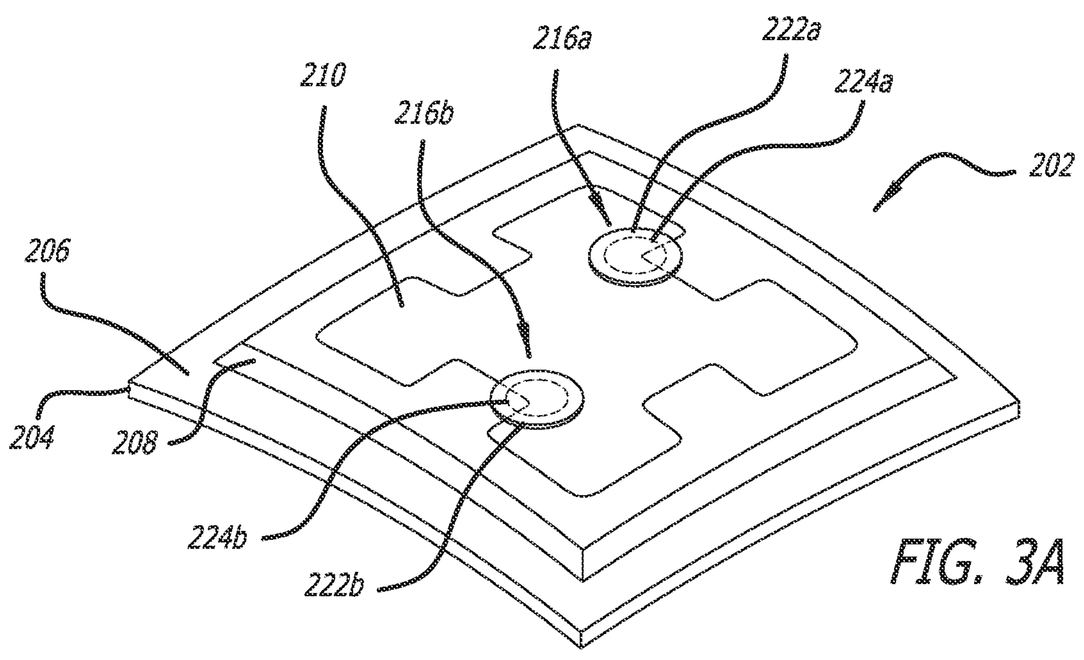
FIG. 3A is an illustration of the conformal antenna of FIG. 2A and associated components including antenna feedthroughs.
Figure 3B:
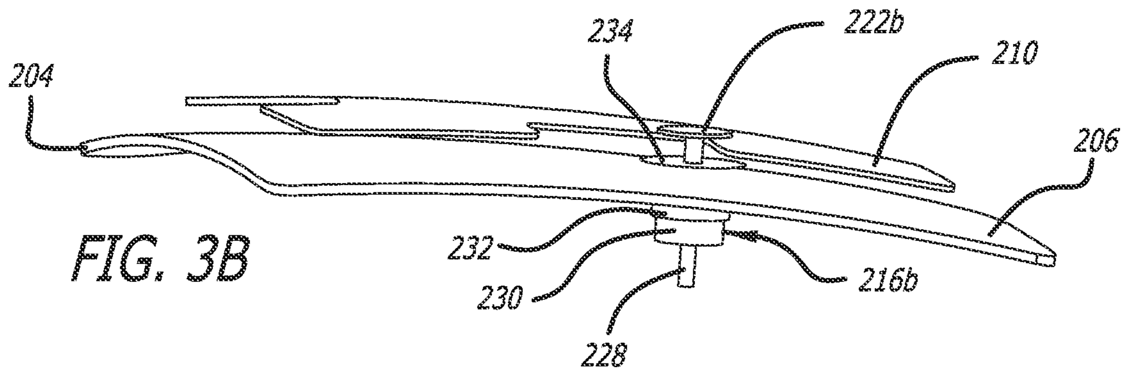
FIGS. 3B and 3C are different perspectives of FIG. 3A with some components of FIG. 3A removed to better illustrate one of the antenna feedthroughs.
Figure 3C:
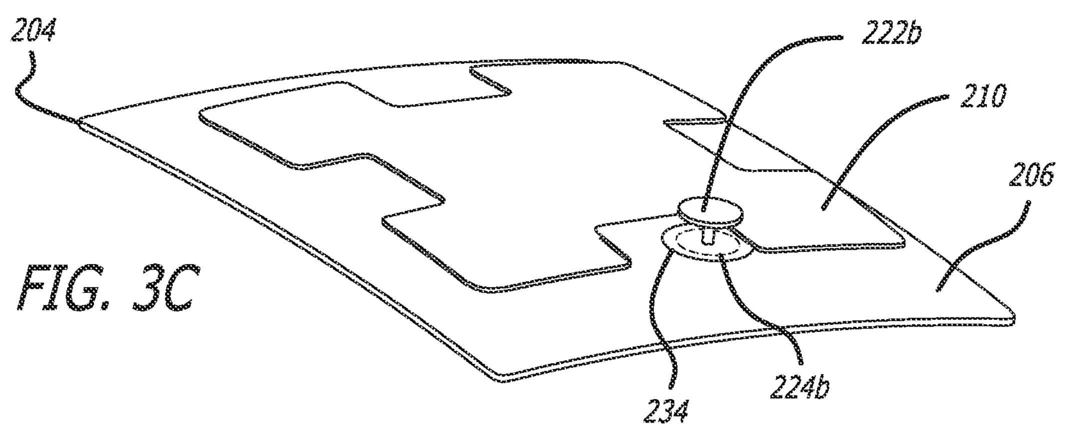

FIG. 3A is an illustration of the conformal antenna 202 and the antenna feedthroughs 216*a*, 216*b* of FIG. 2A. In FIG. 3A all components (e.g., a radiating element 210, a dielectric spacer 208, and a ground plane corresponding to an enclosure 204) of the conformal antenna 202 are shown. FIGS. 3B and 3C are different, rotated perspectives of FIG. 3A. In these figures, only one of the antenna feedthroughs is illustrated and the dielectric spacer 208 is not shown to more clearly illustrate the antenna feedthrough 216*b*. FIGS. 4A and 4B are illustrations of the dielectric spacer 208 and radiating element 210 of a conformal antenna 202. FIG. 4C is an illustration of a radiating element 210 of a conformal antenna 202.

With reference to FIGS. 3A-3C, the ground plane corresponding to the enclosure 204 may be formed of any electrically conductive material. For example, the enclosure 204 may be formed of any biocompatible pure conductive metal, e.g., titanium, or any biocompatible conductive alloy. In some embodiments the portion of the enclosure 204 comprising the outer surface 206 that supports the dielectric spacer 208 has a thickness in the range of 4 mil to 30 mil (~0.1 mm to 0.8 mm). A pair of feedthrough holes 224*a*, 224*b* extend through the enclosure 204 wall and are configured to receive a respective antenna feedthrough 216*a*, 216*b*. As shown in FIGS. 3B and 3C, in some embodiments an antenna feedthrough 216*b* includes a feedthrough wire 228 that extends through a feedthrough hole 224*b*. The feedthrough wire 228 electrically couples to an internal transmission line 212 at one end and to a disc 222*b* at the other end. The disc 222*b* electrically couples to the surface of the radiating element 210. The electrical coupling or connecting of components may be achieved by welding, soldering or gluing (using an electrically conductive glue). One or more hermetic seals 230, 232, 234 are located on each side of the enclosure 204 wall around the feedthrough hole 224*b*.

With reference to FIGS. 4A and 4B, the dielectric spacer 208 may be formed of a biocompatible plastic (e.g., silicone, epoxy, PEEK) with little or no metallic/lossy add-on. In some embodiments, the dielectric spacer 208 has a thickness in the range of 4 mil to 30 mil (~0.1 mm to 0.8 mm). The dielectric spacer 208 is configured to be molded or shaped (by heat) while holding its dielectric properties. The dielectric spacer 208 can be molded or shaped with the same curvature as the outer surface 206 of the enclosure 204 to thereby conform to the top surface of the enclosure.

The dielectric spacer 208 is configured to support the radiating element 210. In some embodiments, the dielectric spacer 208 has a dielectric constant (relative permittivity) that is a fraction of the dielectric constant of tissue at a specific radio frequency. For example, the dielectric constant of the dielectric spacer 208 at a specific radio frequency may be in the range of 2 to 5, while the dielectric constant of the scalp, which covers the implant and therefore loads the antenna, is in the range of 25 to 40 at 2.45 GHz. A pair of holes 226*a*, 226*b* extend through the dielectric spacer 208 and are arranged to align with the feedthrough holes 224*a*, 224*b* of the enclosure 204 and are configured to receive a respective antenna feedthroughs 216*a*, 216*b*.

The radiating element 210 is formed of a conductive material. For example, the radiating element may be formed any biocompatible pure conductive metal, e.g., titanium, or any biocompatible conductive alloy. In some embodiments the radiating element 210 has a thickness in the range of 4 mils to 30 mils (~0.1 mm to 0.8 mm).

With reference to FIG. 4C, in one embodiment the radiating element 210 is characterized by a notched, square shape. This shape is referred to herein as a cloverleaf design. Compared to other radiating elements disclosed below and shown in FIGS. 5A, 5B, and 5C, the cloverleaf design is considered optimal as it provides excellent antenna performance while having a small footprint. In one configuration, the cloverleaf radiating element 210 is approximately 17 mm squared, and includes four notches 402, each positioned midway along the edge of the cloverleaf. Each notch 402 has a depth dimension 404 and an edge dimension 406. In the embodiment of FIG. 4C, the depth dimension is approximately 2.8 mm and the edge dimension is approximately 4.8 mm. Note, the foregoing are example dimensions that resulted from design optimizations carried out on the radiating element to achieve an acceptable size and performance.

The shape and sizes of the radiating element may vary from the cloverleaf configuration of FIG. 4C based on the desired featured designed to the antenna (e.g., the polarization, gain, initial return loss, etc.). FIG. 5A shows a radiating element 510 with a squared configuration with rounded corners. FIG. 5A shows a radiating element 510 with a squared configuration with rounded corners. FIG. 5B shows a radiating element 512 with a rectangular configuration with rounded corners. FIG. 5C shows a radiating element 514 with a squared configuration with rounded corners having a larger radius than those of FIG. 5A. The shape of the radiating element is not limited to the ones shown in the FIGS. 4C, 5A, 5B, and 5C. Any shape that can fit on the outer surface 206 of the enclosure 204 can be used.

With reference to FIGS. 2B and 2C, the dielectric layer 220 is formed of a biocompatible material. For example, the dielectric layer 220 may be a silicon-based glue-sealant. In some embodiments, the dielectric layer 220 has a thickness in the range of 4 mil to 30 mil (~0.1 mm to 0.8 mm). The dielectric layer 220 is configured to be applied over the radiating element 210, the dielectric spacer 208, the portion of the outer surface 206 of the enclosure 204 that supports the radiating element 210 and the dielectric spacer 208, and the antenna feedthroughs 216*a*, 216*b*. For example, the dielectric layer 220 can be over molded onto the antenna assembly, e.g., the radiating element 210, the dielectric spacer 208, the portion of the outer surface 206 of the enclosure 204 that supports the radiating element 210 and the dielectric spacer 208, and the antenna feedthroughs 216*a*, 216*b*. Alternatively, the dielectric layer 220 can be applied as a layer that is held in place over the antenna assembly using a bonding layer such as an epoxy.

Figure 6:
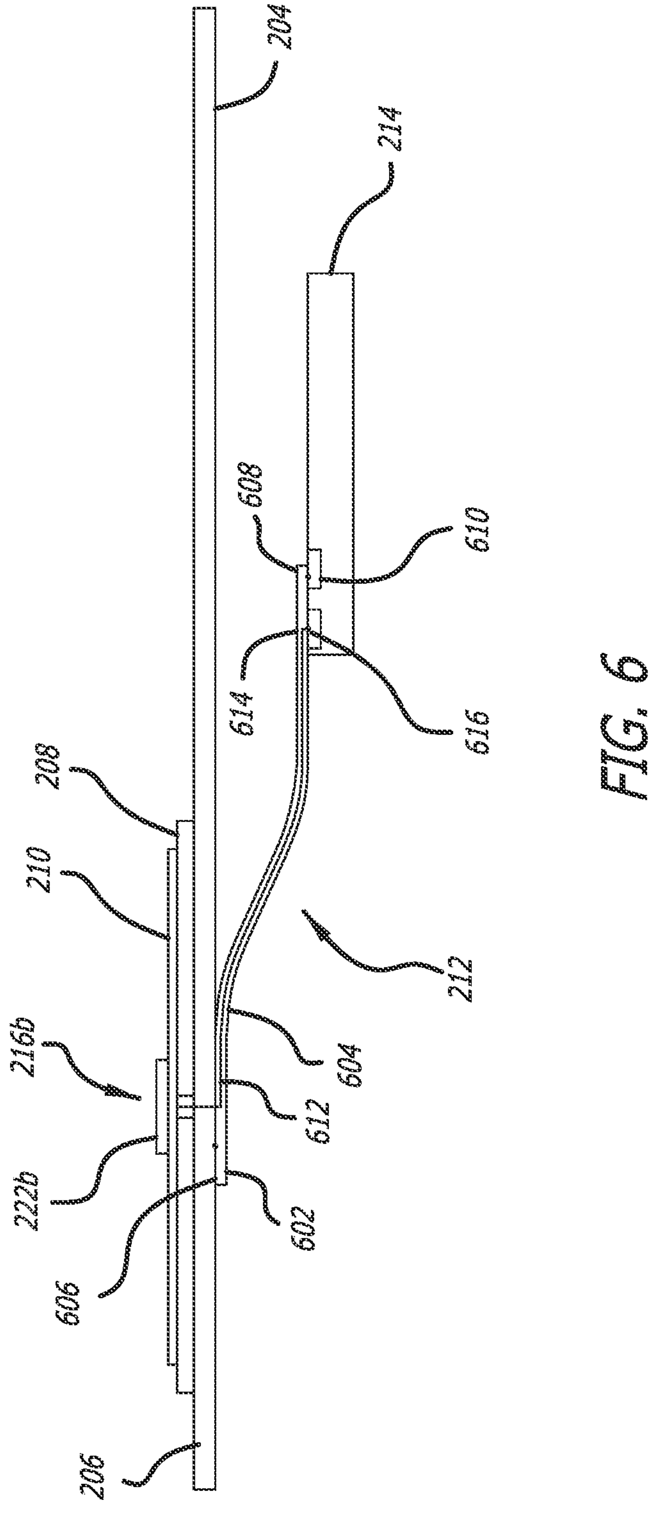
FIG. 6 is a schematic cross-section of components of a conformal antenna coupled to circuitry of the neurostimulator through an internal transmission line.

With reference to FIG. 6, the internal transmission line 212 includes a ground conductor 602 and a signal conductor 604. The ground conductor 602 has a first end 606 and a second end 608. The first end 606 is electrically connected to or coupled to the enclosure 204. To this end, the first end 606 may be welded, soldered or glued (using an electrically conductive glue) to the enclosure 204. The second end 608 is electrically connected to or coupled to a ground terminal 610 of the communication circuitry 214. To this end, the second end 608 may be welded, soldered or glued (using an electrically conductive glue) to the ground terminal 610.

The signal conductor 604 has a first end 612 and a second end 614. The first end 612 includes a pin structure that is configured to mechanically couple with the feedthrough wire 228 of the antenna feedthrough 216*b* and thereby electrically couple with the antenna feedthrough 216*b*. The second end 614 includes a pin structure that is configured to mechanically couple with a signal terminal 616 of the communication circuitry 214 and thereby electrically couple with the communications circuitry. Since the inside the neurostimulator is filled with other essential components, the internal transmission line 212 is configured to have a thin profile and mechanical flexibility.

Figure 7A:
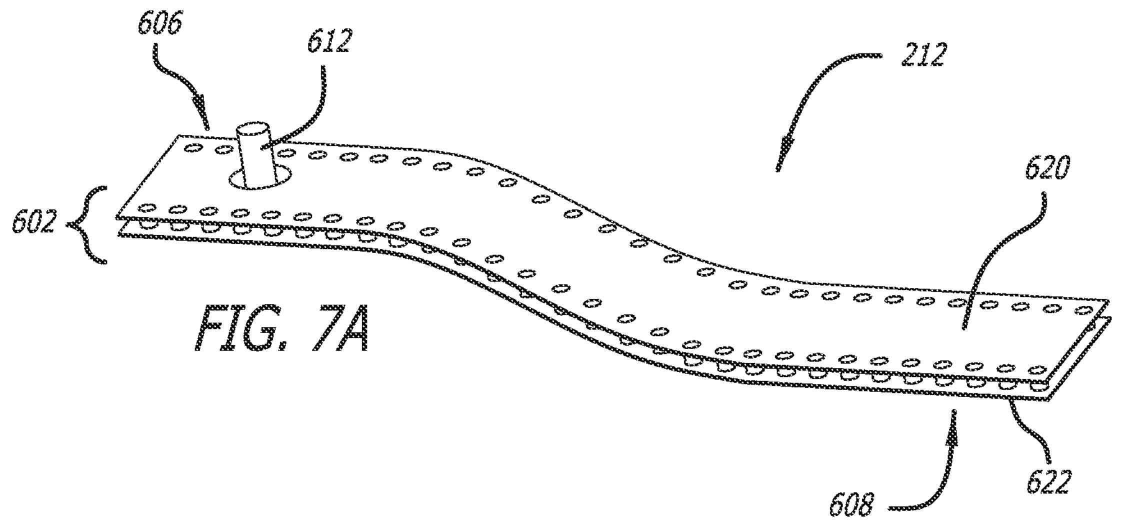
FIGS. 7A and 7B are illustrations of an internal transmission line.
Figure 7B:
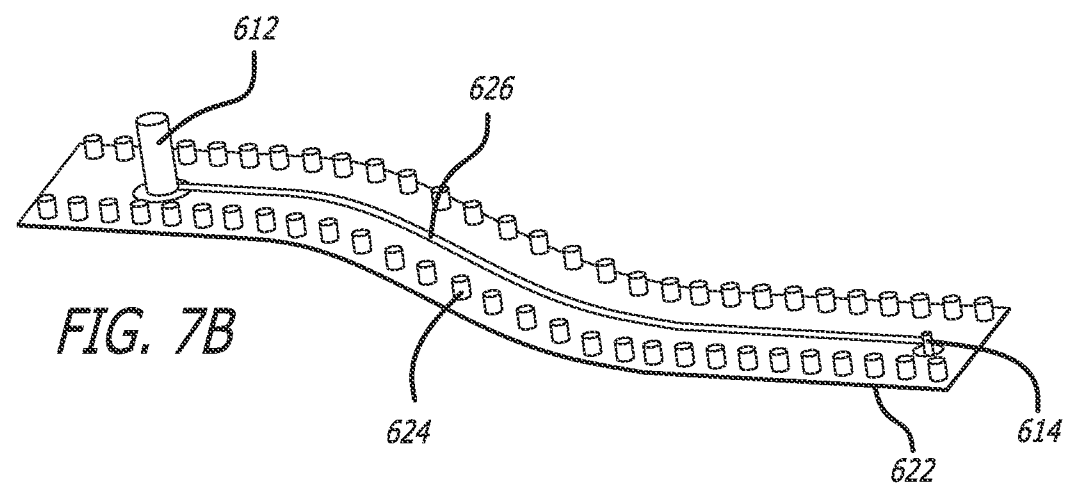
Figure 7C:
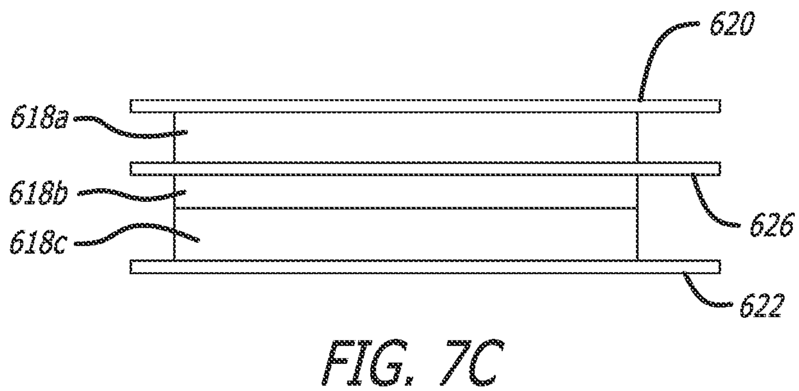
FIG. 7C is a cross section of an internal transmission line.

With reference to FIGS. 7A-7C, in some embodiments the internal transmission line 212 is a stacked arrangement of three flexible layers that include an upper layer 620 of electrically conductive material, a lower layer 622 of electrically conductive material, and an internal layer 626 of electrically conductive material. The electrically conductive material may be copper or another conductive metal or an electrically conductive alloy. Electrically conductive vias 624 extend between and electrically couple the upper layer 620 and the lower layer 622 to form the ground conductor 602. The upper layer 620 of the stacked internal transmission line 212 includes the first end 606 that is electrically coupled to the enclosure 204. The lower layer 622 includes the second end 608 that is electrically coupled to the ground terminal of the communication circuitry 214. The internal layer 626 forms the signal conductor 604. Dielectric layers 618*a*, 618*b*, 618*c* electrically isolate the ground conductor 602 and the signal conductor 604 from each other. In some embodiments, the total thickness of the stacked internal transmission line 212 is between 12-16 mils (305-405 microns).

With reference to FIG. 7C, a first dielectric layer 618*a* isolates the upper layer 620 of electrically conductive material from the internal layer 626 of electrically conductive material. The first dielectric layer 618*a* may be formed of a first flex material and has a thickness in the range of 4 mil to 10 mil (~0.1 mm to 0.25 mm). The first flex material may be, for example, polyimide. A stacked arrangement of a second dielectric layer 618*b* and a third dielectric layer 618*c* isolates the lower layer 622 of electrically conductive material from the internal layer 626 of electrically conductive material. The second dielectric layer 618*b* may be formed of second flex material and has a thickness in the range of 4 mil to 10 mil (~0.1 mm to 0.25 mm). The second flex material may be an adhesive material that functions to adhere the first dielectric layer 618*a* with the third dielectric layer 618*c*. The internal layer 626 of electrically conductive material is thus embedded in dielectric material. The second flex material may be, for example, an epoxy or an acrylic based adhesive. The third dielectric layer 618*c* may be formed of a third flex material and has a thickness in the range of 4 mil to 10 mil (~0.1 mm to 0.25 mm). The third flex material 618*c* may be the same material as the first dielectric layer 618*a*. The third flex material 618*c* may be, for example, polyimide.

Figures 8A, 8B, 8C:
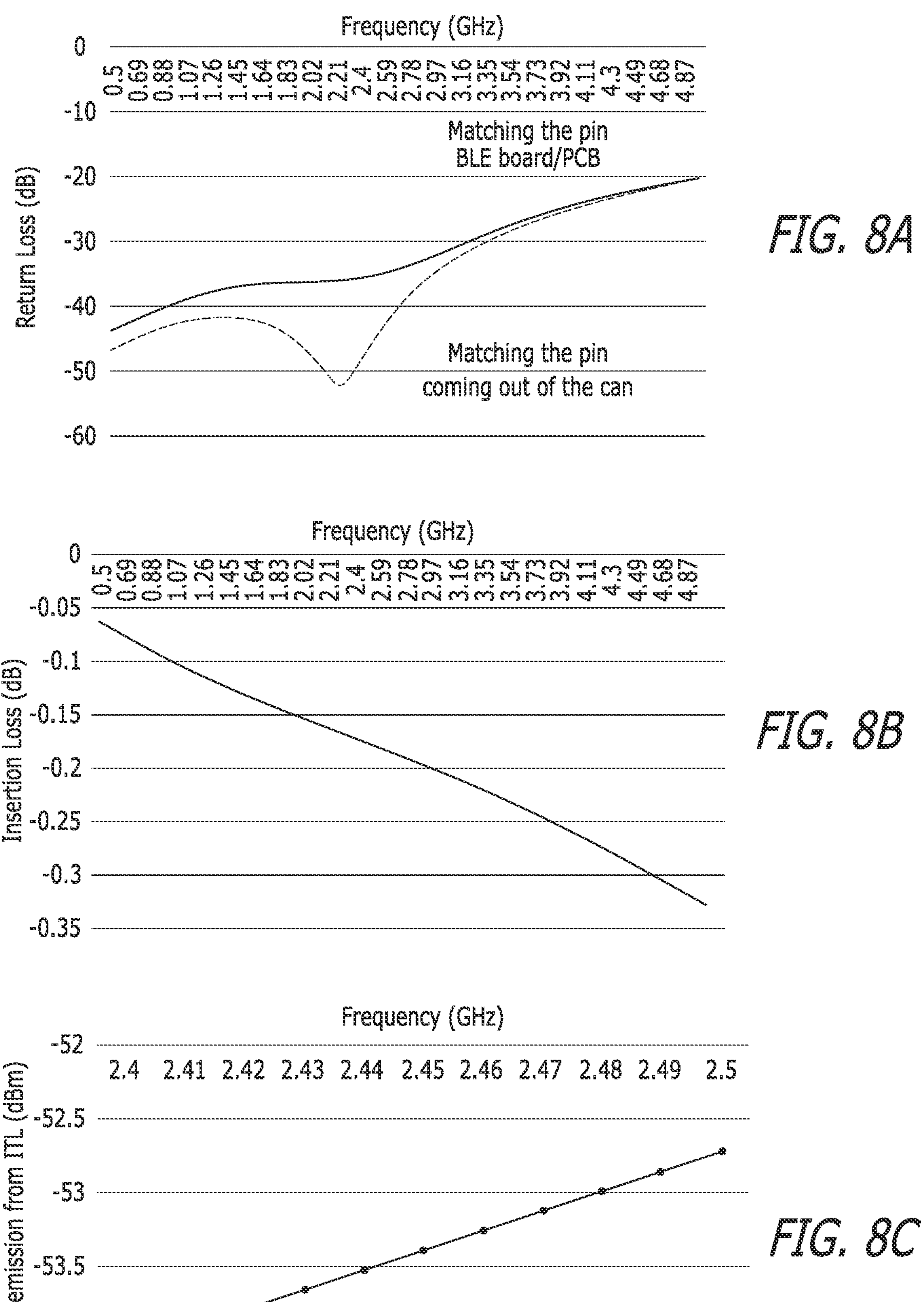
FIG. 8A is an example graph of return loss of an internal transmission line as a function of frequency.
FIG. 8B is an example graph of insertion loss of an internal transmission line as a function of frequency.
FIG. 8C is an example graph of radiated emission or unwanted leakage out of an internal transmission line as a function of frequency.

FIG. 8A is an example graph of return loss of the stacked internal transmission line 212 as a function of frequency. The return loss as a function of frequency of the internal transmission line may vary based on the design of the internal transmission line. FIG. 8B is an example graph of insertion loss of the stacked internal transmission line 212 as a function of frequency. The insertion loss as a function of frequency of the internal transmission line may vary based on the design of the internal transmission line. FIG. 8C is an example graph of radiated emission or unwanted leakage out of the stacked internal transmission line 212 as a function of frequency under simulation. The radiated emission as a function of frequency of the internal transmission line may vary based on the design of the internal transmission line.

Overall, the stacked internal transmission line 212 shows a particularly good performance in a wide frequency range of 500 MHz up to 5 GHz. As shown in FIG. 8A, the return loss of the stacked internal transmission line 212 is better than 20 dB, which is equivalent to less than 1% reflection of the input power at the connection pins of the transmission line. As shown in FIG. 8B, the insertion loss of the stacked internal transmission line 212 is better than −0.3 dB. This means that less than 7% of power is lost in the internal transmission line 212. As shown in FIG. 8C, the radiated emission out of the stacked internal transmission line 212 when the input power to the one side of the transmission line is only 0 dBm (1 mW). The radiated emission is less if −52 dBm (i.e., only 0.0000063 of the input power is emitted).

Figure 9A:
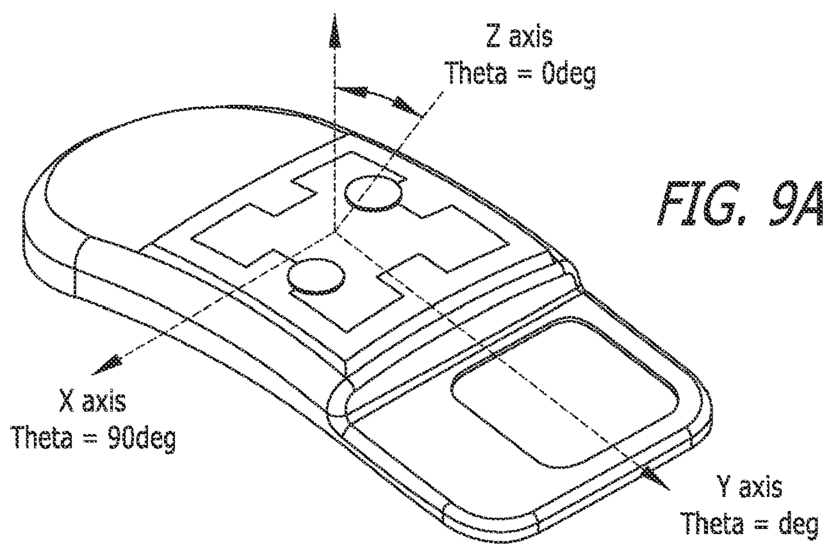
FIG. 9A is an illustration of a neurostimulator with a conformal antenna with reference coordinates.

With reference to FIG. 9A, RF performance of the conformal antenna was tested under simulated implant conditions resembling those shown in FIG. 1. More specifically, the outer surface 206 of the neurostimulator 102 was simulated inside a phantom model representing a patient's head, with the conformal antenna 202 adjacent tissue under the scalp.

Figure 9B:
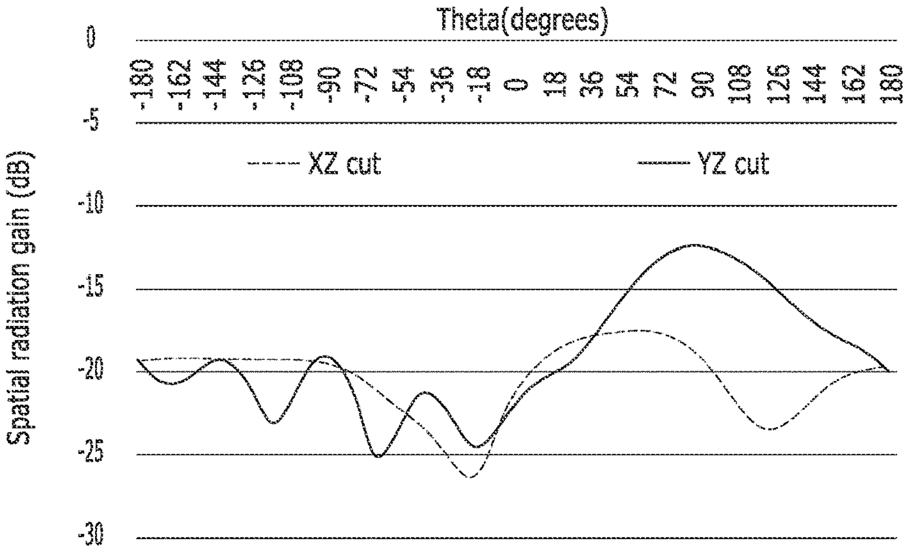
FIG. 9B is an example graph of radiation gain of the conformal antenna of the neurostimulator of FIG. 9A as a function of angular offset relative to different planes (XZ cut and YZ cut) when the neurostimulator is implanted in a patient's skull as shown in FIG. 1.

The peak radiation gain of the antenna was measured under these simulated conditions. Radiation gain shows the percentage/portion of the input power (i.e. from the communication circuitry) that radiates in all directions. All the environmental losses are included in this number. FIG. 9B is an example graph of radiation gain of the conformal antenna of the neurostimulator of FIG. 9A as a function of angular offset relative to different planes (XZ cut and YZ cut), when the neurostimulator is implanted in a patient's skull as shown in FIG. 1. With reference to FIG. 9B, results of the simulated test show the conformal antenna 202 has a peak radiation gain of about −13 dB (i.e., about 5%). The conformal antenna 202 being buried under the skin shows an initial return loss of ~3 dB. The return loss may be improved by the use of a matching network between the communication circuitry 214 and the conformal antenna 202.

Figure 9C:
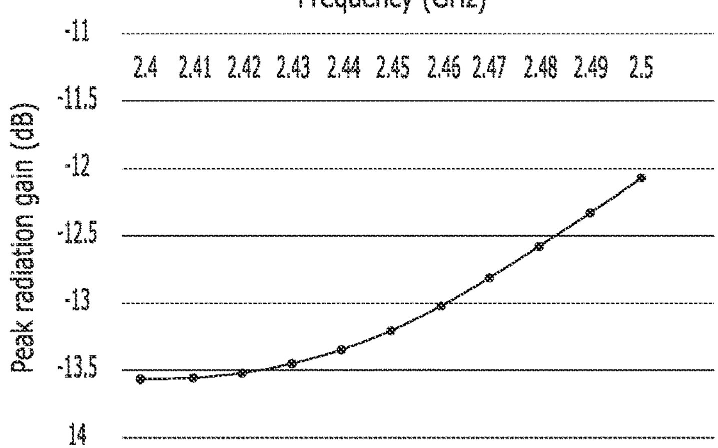
FIG. 9C is an example graph of radiation gain as a function of the conformal antenna of the neurostimulator of FIG. 9A as a function of frequency when the neurostimulator is implanted in a patient's skull as shown in FIG. 1.

The initial return loss of the antenna was also measured under these simulated conditions. Return loss (i.e., matching) gives the percentage of the input power that gets transferred to the antenna. As an example, a return loss of 10 dB is equivalent to 10% reflection of the power back to the communication circuitry. FIG. 9C is an example graph of radiation gain as a function of the conformal antenna of the neurostimulator of FIG. 9A as a function of frequency, when the neurostimulator is implanted in a patient's skull as shown in FIG. 1. With reference to FIG. 9C, results of the simulated test show the peak gain of the conformal antenna 202 varies by about 0.5 dB (i.e., about 10%) within the entire desired frequency band (i.e. Bluetooth). The variation is well within an acceptable range.

External Transmission Line

Figure 10:
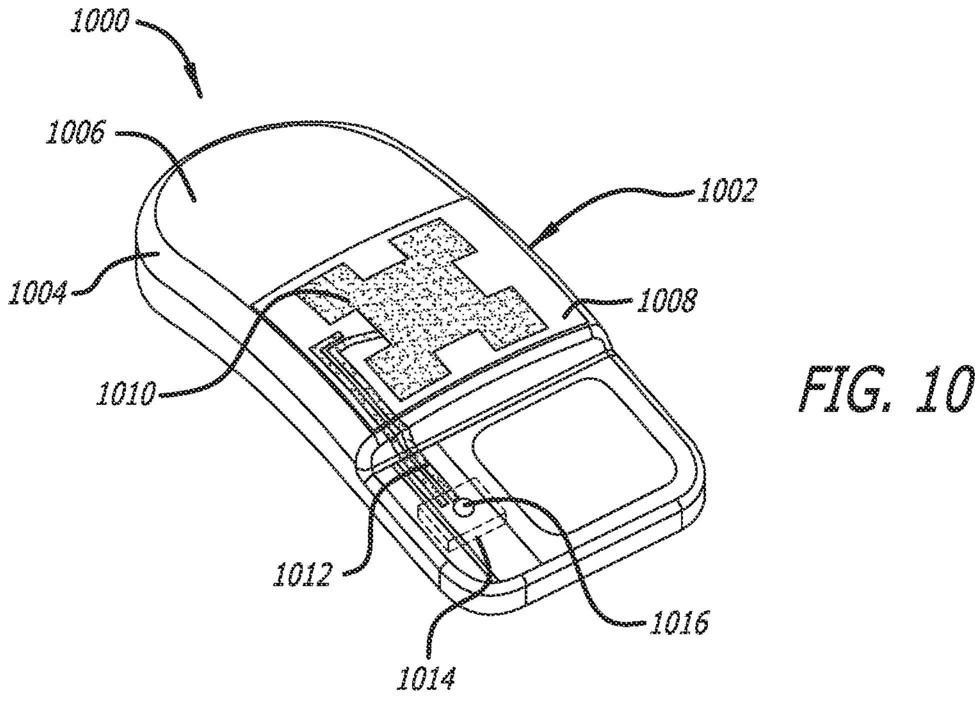
FIGS. 10 and 11 are illustrations of neurostimulator with a conformal antenna and an external transmission line between the antenna and circuitry.
Figure 11:
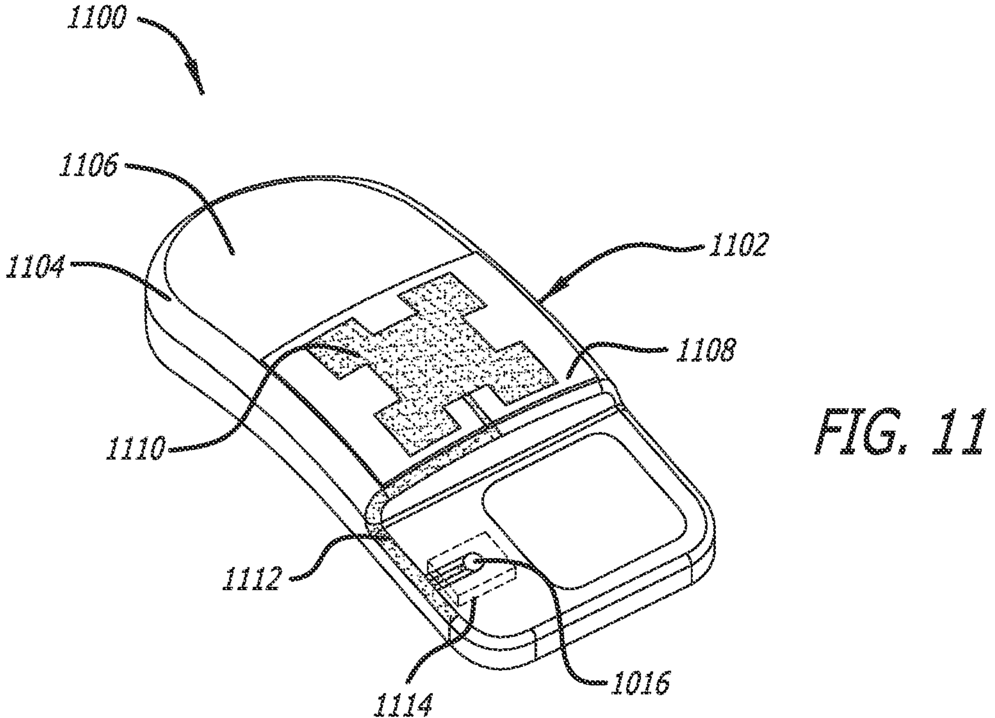

FIGS. 10 and 11 are illustrations of neurostimulators 1000, 1100 with a conformal antenna that includes a radiating element that conforms to an outer surface of the enclosure and is coupled to communication circuitry inside the enclosure by an external transmission line that conforms to, and extends along, an outer surface of the enclosure.

With reference to FIGS. 10 and 11, the neurostimulator 1000, 1100 includes an enclosure 1004, 1104 having an outer surface 1006, 1106. The enclosure 1004, 1104 contains electronic circuitry. For example, communication circuitry 1014, 1114 may be housed within the enclosure 1004, 1104. The conformal antenna 1002, 1102 includes a ground plane corresponding to the enclosure 1004, 1104, a dielectric spacer 1008, 1108 that conforms to, and is supported by, a portion of the outer surface of the enclosure, and a radiating element 1010, 1110 that conforms to, and is supported by a portion of the dielectric spacer. An external transmission line 1012, 1112 conforms to, and is supported by a portion of the dielectric spacer that extends along the outer surface 1006, 1106 of the enclosure 1004, 1104 to a location remote from the radiating element 1010, 1110. In some embodiments, the external transmission line 1012, 1112 is an electrical trace. A dielectric layer (not shown) overlays the external transmission line 1012, 1112, the radiating element 1010, 1110, the dielectric spacer 1008, 1108, and a portion of the outer surface 1006, 1106 of the enclosure 1004, 1104. An antenna feedthrough 1016, 1116 extends through the enclosure 1004, 1104 wall at the location remote from the radiating element 1010, 1110. The external transmission line 1012, 1112 electrically coupled to the antenna feedthrough 1016, 1116 to thereby couple the radiating element 1010, 1110 to the communication circuitry 1014, 1114.

With reference to FIGS. 10, 12, and 12A, in some embodiments the external transmission line 1012 extends within a trench or channel 1202 formed within the dielectric spacer 1008. The channel 1202 extends from a location on the dielectric spacer 1008 beneath the radiating element 1010 (where the external transmission line 1012 couples to the radiating element 1010) to the location remote from the radiating element 1010 (where the external transmission line 1012 couples to the antenna feedthrough 1016). A filler 1204 encapsulates the external transmission line 1012 within the channel. The filler 1204 may be a plastic-based an insulator that functions to hold the external transmission line 1012 in place. In this embodiment, because the external transmission line 1012 lies in a channel 1202 in a plane different from the plane in which the radiating element 1010 lies, the external transmission line 1012 is not co-planar with the radiating element 1010. The channel 1202 allows for the control of the impedance of the external transmission line 1012 so that more of the signals from the communication circuitry reach to the radiating element 1010.

With reference to FIGS. 13A and 13B, in some embodiments a conformal antenna 1302 includes a rectangular structure 1314*a*, 1314*b* that is coplanar with the radiating element 1310 and functions as an extension of the ground plane corresponding to the enclosure 1304. The rectangular structure 1314*a*, 1314*b* is supported by and conforms to a portion of the dielectric spacer 1308 that is spaced apart from the portion of the dielectric spacer that supports the radiating element 1310. Thus, the rectangular structure 1314*a*, 1314*b* is co-planar with the radiating element 1310. The rectangular structure 1314*a*, 1314*b* electrically couples to the ground plane corresponding to the enclosure 1304 through a feed-through (not visible) underneath the rectangular structure.

The external transmission line 1312 extends from the radiating element 1310 to a region adjacent to and spaced apart from the rectangular structure 1314*a*, 1314*b*. The terminal end 1320 of the external transmission line 1312 electrically couples to communication circuitry (not shown) through a feed-through (not visible) underneath the external transmission line. With reference to FIG. 13A, in some embodiments, the rectangular structure 1314*a* spans a distance 1322 of the dielectric spacer 1308 greater than the radiating element 1310. The rectangular structure 1314*a* has a slot 1316 that exposes a portion of the dielectric spacer 1308 and the external transmission line 1312 extends from the radiating element 1310 into and along a length of the slot while maintaining separation from the rectangular structure 1314*a*. With reference to FIG. 13B, in some embodiments, the rectangular structure 1314*b* spans a distance 1324 of the dielectric spacer 1308 less than the radiating element 1310. The rectangular structure 1314*b* has a notch 1326 and the external transmission line 1312 extends from the radiating element 1310 along a length of the notch while maintaining separation from the rectangular structure 1314*b*. These rectangular structure 1314*a*, 1314*b* allow for the control of the impedance of the external transmission line 1312 so that more of the signals from the communication circuitry reach to the radiating element 1310.

In the configurations of FIGS. 13A and 13B, the dielectric spacer 1308 is of uniform thickness and the radiating element 1310, external transmission line 1312, and rectangular structure 1314*a*, 13*a*4*b* are metal printed onto the dielectric spacer 1308. The resulting structure is then secured to the enclosure 304.

Location of Conformal Antenna

Figure 14A:
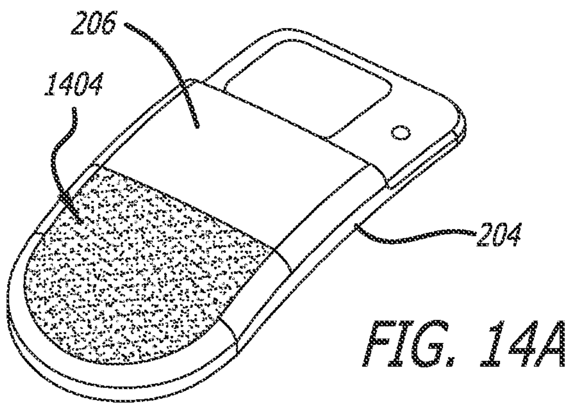
FIGS. 14A-14C are illustrations of different configurations of conformal antenna with radiating elements at different locations on an enclosure of a neurostimulator.
Figure 14B:
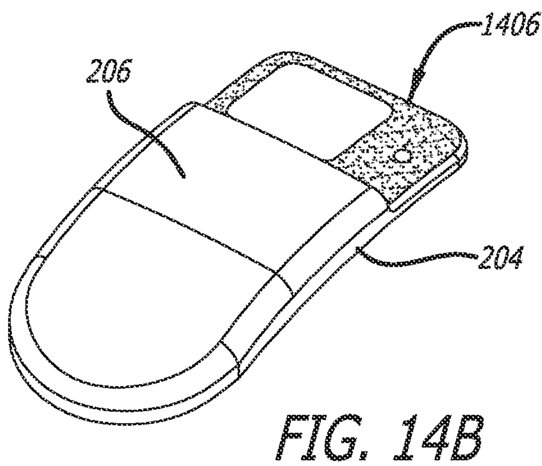
Figure 14C:
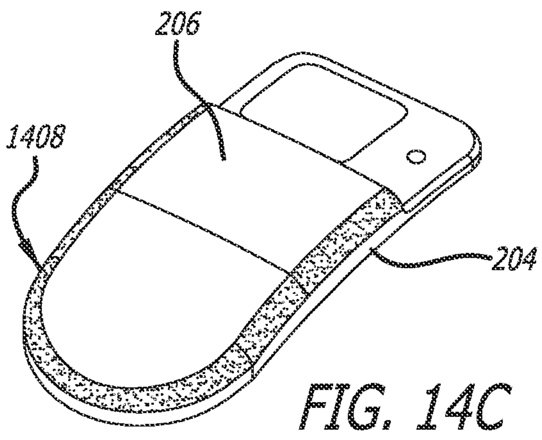

While the conformal antenna 202 primarily described throughout this disclosure has a radiating element 210 on a particular segment, e.g., a middle segment, of the outer surface 206 of the enclosure 204, a conformal antenna may have a radiating element located on other segments of the outer surface of the enclosure. For example, with reference to FIG. 14A a conformal antenna may have a radiating element on a first end segment 1404 of the outer surface 206 of the enclosure 204. With reference to FIG. 14B, a conformal antenna may have a radiating element on a second end segment 1406 of the outer surface 206 of the enclosure 204. With reference to FIG. 14C, a conformal antenna may have a radiating element on a perimeter segment 1408 of the outer surface 206 of the enclosure 204.

Assembly of Neurostimulator with Conformal Antenna

Following is an example process of assembling a neurostimulator with a conformal antenna of the type shown in FIG. 2A.

A top subassembly of the neurostimulator is assembled. To this end, a top half of an enclosure 204 is obtained. The top half of the enclosure 204 has an outer surface 206 with curved, non-linear cross-section profiles and installed antenna feedthrough 216*a*, 216*b*. A radiating element 210 having curved, non-linear cross-section profiles and a surface shape generally conforming to the contour of the outer surface 206 of enclosure 204 is obtained. A dielectric spacer 208 having curved, non-linear cross-section profiles and a surface shape generally conforming to the contour of the outer surface 206 of the enclosure 204, and with and feedthrough holes 226*a*, 226*b* that match the locations of the antenna feedthroughs 216*a*, 216*b* is obtained.

The radiating element 210 is adhered to the dielectric spacer 208. The radiating element 210 and dielectric spacer 208 are adhered to the outer surface 206 of the enclosure 204 such that the holes 226*a*, 226*b* align with the antenna feedthroughs 216*a*, 216*b*. Electrical connections are made between the feedthrough wires 228 and the radiating element 210 using the disc 222*a*, 222*b*. A dielectric layer 220 is adhered to the outer surface 206 of the enclosure to cover the assembled radiating element 210 and dielectric spacer 208. A first internal transmission line 212*a* is electrically connected at one end to a feedthrough wire 228 of a first antenna feedthrough 216*a*. A second internal transmission line 212*b* is electrically connected at one end to a feedthrough wire 228 of a second antenna feedthrough 216*b*.

A bottom subassembly of a neurostimulator is obtained. The bottom subassembly includes a bottom half of the enclosure and holds various electronics, including a first communication circuitry 214*a* and a second communication circuitry 214*b*. The first internal transmission line 212*a* of the top subassembly is electrically connected at its other end to the first communication circuitry 214*a*. The second internal transmission line 212*b* is electrically connected at its other end the second communication circuitry 214*b*. Other connections between the top and bottom subassemblies are made and the top and bottom portions of the enclosure 204 are secured together to form the neurostimulator.

Comparison to Traditional Patch Antenna

Compared to a traditional antenna, the conformal antenna disclosed herein has some unique features. The conformal antenna is implanted in the skull while a thick layer of skin is placed over the antenna (i.e., the antenna is being loaded by the skin). The radiating element and the ground plane of the conformal antenna are both non-planar and have a similar curvature. The conformal antenna (and external transmission line if presented) is covered by a silicon-based sealant/glue so that bodily fluid and/or blood do not contact the radiating element (and external transmission line if presented), and do not penetrate the enclosure via the feedthrough beneath the radiating element to contact an internal transmission line (if present).

Figure 15A:
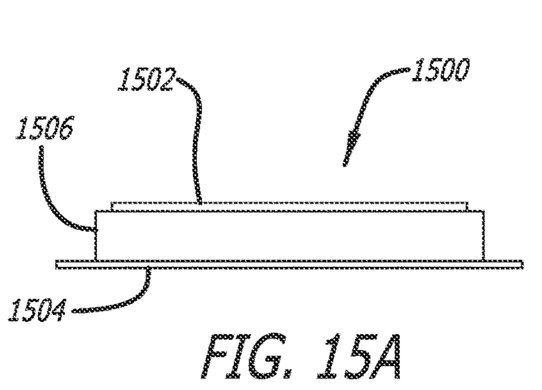
FIGS. 15A and 15B are schematic illustration of a traditional patch antenna.
Figure 15B:
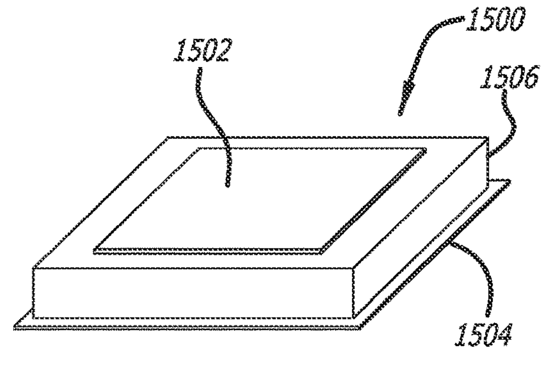

FIGS. 15A and 15B show a traditional patch antenna 1500 having two metallic layers 1502, 1504 with a substrate 1506 separating two layers. Patch antennas are usually a half-wavelength by a half-wavelength shape. The wavelength is defined as the effective wavelength of the antenna on the designated substrate as the wavelength at the center frequency in air divided by the effective permittivity of the substrate (for example, the effective wavelength of @2.45 GHz for a substrate with permittivity of 2, is about 85 mm, so an ideal patch antenna would be about 40 mm by 40 mm).

Figure 16:
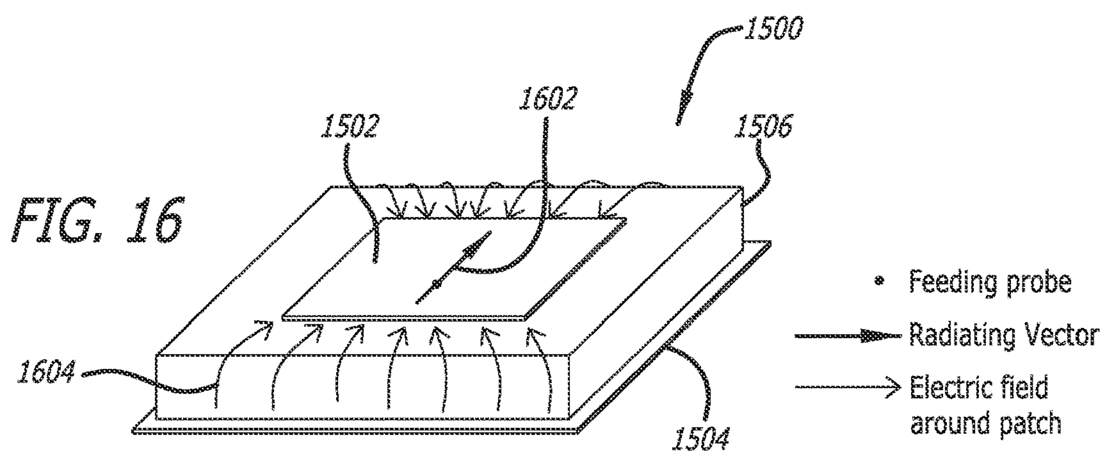
FIG. 16 is a schematic illustration of active electric fields generated by the patch antenna of FIGS. 15A and 15B.

With reference to FIG. 16, in a traditional patch antenna 1500, the active electric field 1604 generating the radiating vector 1602 is mainly confined by the substrate 1506. The active electric field 1604 on the sides of the patch antenna 1500 form a constructive radiating vector 1602. Since the substrate 1506 contains the majority of the active electric field 1604, the dielectric properties of the substrate play an important role in determining the resonance frequency of the patch antenna 1500.

Figure 17:
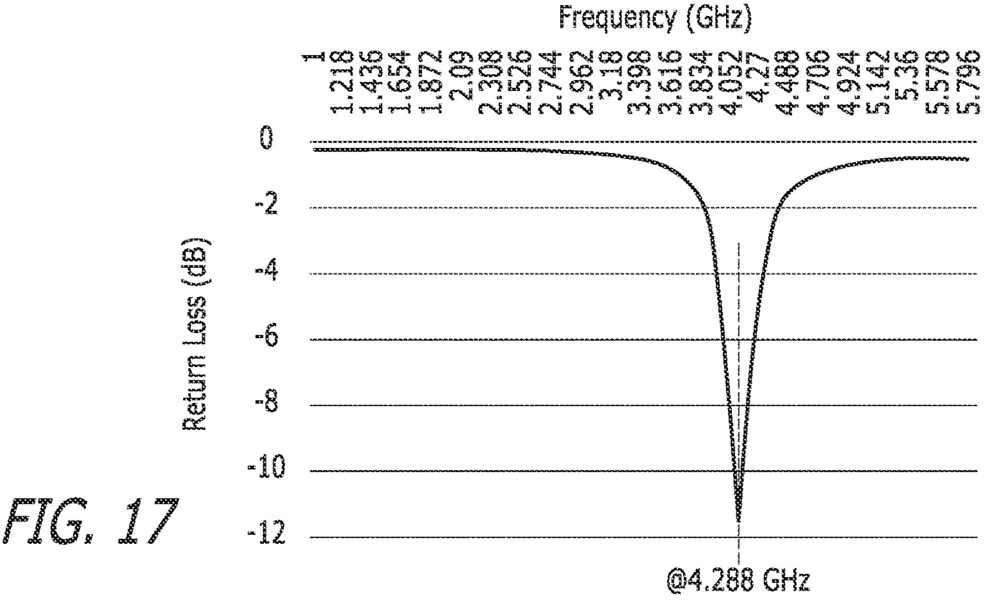
FIG. 17 is a graph of return loss as a function of frequency for the patch antenna of FIGS. 15A and 15B.

With reference to FIG. 17, it can be seen that the traditional patch antenna provides a peak return loss of 12 dB at 4.288 GHz under simulation in air. However, at a desired Bluetooth frequency of 2.45 GHZ, the return loss is only 0.1 dB. In order for antenna to be useable in a system, the initial return loss at the desired frequency should be at least 2 dB or better. Thus, the traditional patch antenna is unsuitable for 2.45 GHz.

With reference to FIGS. 18A and 18B, the conformal antenna 202 disclosed herein is designed and optimized while placed in a particular operating environment (implanted under skin), therefore, the operating concept behind the conformal antenna 202 is significantly different than that of a traditional patch antenna operating in air.

The skin 1802 can be modeled as a lossy dielectric. The dielectric constant of the skin 1802 at a desired frequency (e.g., 2.45 GHz) is over 20 while the dielectric spacer 208 of the conformal antenna 202 has a relative permittivity of about 2-3. As a result, the layer of the skin 1802 is the dominant material characterizing the performance of the conformal antenna 202. Similarly, the skin 1802 has an estimated conductivity of 1 S/m while this number essentially is close to zero for regular RF substrates.

FIG. 19 shows the simplified electric field distribution of the conformal antenna 202 in a desired operating environment (implanted under skin) 1802. Since the conformal antenna 202 is loaded with skin 1802, which has a much higher dielectric constant than air and the dielectric spacer 208, the active electric field 1804 generating the radiating vector 1806 is surrounds and covers the radiating element 210. This is distinct from a patch antenna of FIG. 16, where the active electric field 1604 is confined on two edges along the radiating element 1502.

FIG. 20 shows the return loss of a conformal antenna 202 when a layer of skin covers the antenna. The initial return loss of this conformal antenna 202 at the desired frequency (e.g., 2.45 GHZ) is more than 2 dB.

The various aspects of this disclosure are provided to enable one of ordinary skill in the art to practice the present invention. Various modifications to exemplary embodiments presented throughout this disclosure will be readily apparent to those skilled in the art, and the concepts disclosed herein may be extended to other magnetic storage devices. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. An implantable medical device (IMD) configured for implant in a body, the IMD comprising:
- an enclosure that houses communication circuitry, and comprising an outer surface configured to be oriented in a direction facing the exterior of the body and to be placed adjacent tissue;
- an antenna including:
  - a ground plane corresponding to the enclosure;
  - a dielectric spacer that conforms to the outer surface of the enclosure; and
  - a radiating element that conforms to the dielectric spacer;
- a dielectric layer that overlays the radiating element and the dielectric spacer;
- a transmission line outside the enclosure and electrically coupled between the radiating element and the communication circuitry; and
- a rectangular structure that is co-planar with and spaced apart from the radiating element, conformed to a portion of the dielectric spacer, and electrically coupled to the ground plane through a feedthrough,
- wherein the transmission line extends from the radiating element to a region adjacent to and spaced apart from the rectangular structure and the rectangular structure has a slot that exposes a portion of the dielectric spacer, and the transmission line is spaced apart from the rectangular structure and extends into and along a length of the slot.

2. The IMD of claim 1, wherein the ground plane corresponding to the enclosure is non-planar.

3. The IMD of claim 1, wherein the radiating element is non-planar.

4. The IMD of claim 1, wherein the outer surface of the enclosure that supports the dielectric spacer is characterized by a non-linear profile having a first curvature and the radiating element is characterized by a non-linear profile having a second curvature that generally corresponds to the first curvature.

5. The IMD of claim 1, wherein the radiating element is characterized by a notched, rectangular shape.

6. The IMD of claim 1, wherein the radiating element is formed of a conductive material and has a thickness in a range of a 4 mils to 30 mils (~0.1 mm up to 0.8 mm).

7. The IMD of claim 1, wherein the enclosure is formed of a conductive material and the portion of the enclosure beneath the dielectric spacer has a thickness in a range of a 4 mils to 30 mils (~0.1 mm up to 0.8 mm).

8. The IMD of claim 1, wherein the dielectric spacer has a dielectric constant at a specific radio frequency that is a fraction the dielectric constant of tissue at the specific radio frequency.

9. The IMD of claim 8, wherein the dielectric constant of the dielectric spacer is in a range of 2 to 5.

10. The IMD of claim 1, wherein the dielectric spacer is formed of a biocompatible plastic and has a thickness in a range of a 4 mils to 30 mils (~0.1 mm up to 0.8 mm).

11. The IMD of claim 1, wherein the dielectric layer is formed of a biocompatible material and has a thickness in a range of a 4 mils to 30 mils (~0.1 mm up to 0.8 mm).

12. The IMD of claim 1, wherein the antenna operates in a frequency band in a range of at least one of 2.4 GHz to 2.5 GHz and from 5.15 GHz to 5.85 GHz.

13. The IMD of claim 1, wherein the antenna has a peak radiation gain in a range of −10 dB to −13 dB when implanted under skin.

14. The IMD of claim 13, wherein the antenna operates in a first frequency band in a range of 2.4 GHz to 2.5 GHZ, and in a second frequency band in a range of 5.15 GHZ to 5.85 GHz.

15. The IMD of claim 1, further comprising second communication circuitry and a second transmission line, wherein the second transmission line is electrically coupled between the radiating element and the second communication circuitry.

16. The IMD of claim 1, further comprising at least one antenna feedthrough electrically coupled to the communication circuitry, and that extends through the enclosure at a location remote from the radiating element, wherein the transmission line is electrically coupled to the communication circuitry through the at least one antenna feedthrough.

17. The IMD of claim 1, wherein the dielectric spacer, the transmission line, and the dielectric layer extend together along the outer surface of the enclosure to a location remote from the radiating element.

* * * * *